(12) United States Patent
Klee

(10) Patent No.: US 6,787,361 B1
(45) Date of Patent: Sep. 7, 2004

(54) CLINICAL ASSAY CALIBRATION ADJUSTMENT METHOD

(75) Inventor: George G. Klee, Rochester, MN (US)

(73) Assignee: Mayo Foundation for Medical Education and Research, Rochester, MN (US)

(*) Notice: Subject to any disclaimer, the term of this patent is extended or adjusted under 35 U.S.C. 154(b) by 293 days.

(21) Appl. No.: 09/853,867

(22) Filed: May 11, 2001

Related U.S. Application Data

(60) Provisional application No. 60/203,565, filed on May 11, 2000.

(51) Int. Cl.[7] .......................... G01N 31/00; G06F 19/00
(52) U.S. Cl. .............................. 436/8; 436/43; 702/19; 702/22; 702/32
(58) Field of Search .................. 436/8, 43; 702/19, 702/22, 30, 32

(56) References Cited

U.S. PATENT DOCUMENTS 5,230,863 A * 7/1993 Salpeter ..................... 422/67

OTHER PUBLICATIONS

American Urological Association, "Early detection of prostate cancer," American Urological Association Policy Statements, Board of Directors, Jan. 1992—http://www.auanet.org/aboutaua/policy statements.

Consensus Development Conference Panel, "Diagnosis and Management of Asymptomatic Primary Hyperparathyroidism: Consensus Development Conference Statement," *Ann. Intern. Med.*, 1991, 114(7):593–597.

Department of Health and Human Services, Part II, "Medicare, Medicaid and CLIA Programs; Regulations Implementing the Clinical Laboratory Improvement Amendments of 1988 (CLIA)," *Federal Register*, Feb, 28, 1992, 57(40):7002–7186.

Grundy, "National Cholesterol Education Program—Second Report of the Expert Panel on Detection, Evaluation, and Treatment of High Blood Cholesterol in Adults (Adult Treatment Panel II)," *Circulation*, 1994, 89(3):1331–1363.

Jacobsen et al., "Predictive Properties of Serum Prostate–Specific Antigen Testing in a Community–Based Setting," *Arch. Intern. Med.*, 1996, 156:2462–2468.

Klee, "A conceptual model for establishing tolerance limits for analytic bias and imprecision based on variations in population test distributions," *Clin. Chim. Acta*, 1997, 260:175–188.

Klee et al., "Analytic bias specifications based on the analysis of effects on performance of medical guidelines," *Scand. J. Clin. Lab. Invest.*, 1999, 59:509–512.

Mettlin et al., "Defining and Updating the American Cancer Society Guidelines for the Cancer–Related Checkup: Prostate and Endometrial Cancers," *CA Cancer J. Clin.*, 1993, 43:42–46.

Smith and Kroft, "Optimal Procedures for Detecting Analytic Bias Using Patient Samples," *Am. J. Clin. Pathol.*, 1997, 108:254–268.

Westgard et al., "Quality Management," *Tietz Textbook of Clinical Chemistry*, 1998, 3rd Edition, Burtis et al. (eds.), W.B. Saunders Company, Philadelphia, Chapter 17, pp. 548–592.

* cited by examiner

*Primary Examiner*—Maureen M. Wallenhorst
(74) *Attorney, Agent, or Firm*—Fish & Richardson P.C., P.A.

(57) ABSTRACT

A method for calibrating a clinical laboratory analytical instrument that includes generating control pool data from a commutable control pool, wherein the control pools have target analyte values for an assay, generating patient specimen data from a distribution of test values from patient specimens, determining tolerance limits from the control pool data and the patient specimen data; and adjusting the calibration of the instrument with respect to the tolerance limits.

30 Claims, 9 Drawing Sheets

CLINICAL ASSAY CALIBRATION ADJUSTMENT METHOD

RELATED APPLICATIONS

This application claims the benefit of prior U.S. provisional application No. 60/203,565, filed on May 11, 2000.

TECHNICAL FIELD

This invention relates to procedures for tracking clinical laboratory measurements and calibrating measurement systems to ensure measurement reliability.

BACKGROUND

The Federal Clinical Laboratory Improvement Act (CLIA) requires that clinical laboratories run quality controls and participate in proficiency testing programs. CLIA has defined relatively wide tolerance limits for proficiency testing programs. Absolute set points are not defined for most controls, so most clinical laboratories establish their own set-point values based on the average of 15 to 20 measurements and track precision around these arbitrarily defined set points.

Most clinical laboratory measurements are performed with reagents and instruments that are manufactured by commercial companies. The processes used to manufacture these materials have multiple sources of variability, which result in final products that produce test measurements that differ both between instruments and within instruments across calibrations and across batches of reagents. Manufacturing processes for many laboratory measurement systems typically have tolerance limits of about ±10%. Efforts to reduce the tolerance limits typically are complex and increase the cost of manufacturing the measurement systems.

The median values for large distributions of patient test values are remarkably constant over time, assuming that the measurement systems and the patient demographics are relatively constant. Some laboratory measurements vary with pre-analytic variables such as food supplementation, and collection and transport conditions, but, if the number of measurements is large, most of these factors average out and do not cause major shifts in the distributions of test values. If specimens are collected from patients with characteristics different from the general population, such as, for example, patients from oncology, surgery, intensive care units, and pediatrics, the test distribution may change. When these differences are known, the test values can be mathematically adjusted to normalize the test distributions.

However, absent special circumstances, clinicians are seldom informed about changes in analytic bias or "setpoint" in clinical laboratory measurements, and their diagnostic processes cannot be readily adjusted to account for these level differences. Even if a laboratory is aware of a change in bias, there generally is no easy way to correct the problem unless the reagents and/or instruments used to make the clinical measurements are changed.

SUMMARY

The combination of the wide control limits and arbitrarily set target values substantially reduces the value of un-assayed control materials in monitoring long-term analytic bias in a clinical laboratory. As a result, actual patient test values used in clinical decisions are not directly tracked, and their constancy is not controlled. These measurement variations may significantly impact treatment protocols in a patient population.

The present invention is directed to a method for more tightly controlling the distributions of analytic test values reported to clinicians by adjusting assay set points using a combination of traceable control materials and patient test values. The present invention also is directed to a computer readable medium encoded with a computer program arranged to execute such a method.

In one embodiment, the invention is a method for calibrating a clinical laboratory analytical instrument, including generating control pool data from a commutable control pool, wherein the control pools have target analyte values for an assay, generating patient specimen data from a distribution of test values from patient specimens; determining tolerance limits from the control pool data and the patient specimen data; and adjusting the calibration of the instrument with respect to the tolerance limits.

In a second embodiment, the invention provides a computer readable medium encoded with a computer program, the program being arranged such that, when the program is executed, a computer performs the acts of generating control pool data from a commutable control pool, wherein the control pools have target analyte values for an assay, generating patient specimen data from a distribution of test values from patient specimens; determining tolerance limits from the control pool data and the patient specimen data; and adjusting the calibration of the instrument with respect to the tolerance limits.

In a third embodiment, the invention is a chemical analyzer including a processor responsive to a computer program, the program being arranged such that, when the program is executed, the processor performs the acts of generating control pool data from a commutable control pool, wherein the control pools have target analyte values for an assay, generating patient specimen data from a distribution of test values from patient specimens; determining tolerance limits from the control pool data and the patient specimen data; and adjusting the calibration of the instrument with respect to the tolerance limits.

In a fourth embodiment, the invention is a clinical analytical instrumentation system including a central computer and a network of chemical analyzers, wherein at least one of the central computer and the analyzers includes a processor responsive to a computer program. The program is arranged such that, when the program is executed, the processor performs the acts of generating control pool data from a commutable control pool, wherein the control pools have target analyte values for an assay, generating patient specimen data from a distribution of test values from patient specimens, determining tolerance limits from the control pool data and the patient specimen data; and adjusting the calibration of the instrument with respect to the tolerance limits.

In a fifth embodiment, the invention is a method for analyzing data in an analytical laboratory, wherein the laboratory includes a central computer networked with at least one chemical analyzer. The method includes transferring assay data from the analyzers to the central computer, wherein a processor in the central computer generates control pool data from a commutable control pool, wherein the control pools have target analyte values for an assay, generates patient specimen data from a distribution of test values from patient specimens, determines tolerance limits from the control pool data and the patient specimen data; and adjusts the calibration of at least one chemical analyzer with respect to the tolerance limits.

The inventive method has the potential for markedly improving the clinical performance of automated laboratory measurement systems by both reducing the fluctuations in analytic bias and by anchoring these assays to traceable reference standards. If this procedure is accepted by the appropriate governing and licensure groups, (such as the U.S. Food and Drug Agency), it could provide a more cost-effective method for assay standardization. The tight industrial manufacturing processes required to assure equivalent levels of accuracy for an analytical laboratory instrument would generally be much more expensive than this method for calibration adjustment. The method of the invention has the added advantage of providing post-manufacturing confirmation of the performance of the measured systems in the medical center laboratories.

The details of one or more embodiments of the invention are set forth in the accompanying drawings and the description below. Other features, objects, and advantages of the invention will be apparent from the description and drawings, and from the claims.

DESCRIPTION OF DRAWINGS

Like reference symbols in the various drawings indicate like elements.

DETAILED DESCRIPTION

Figure 1:
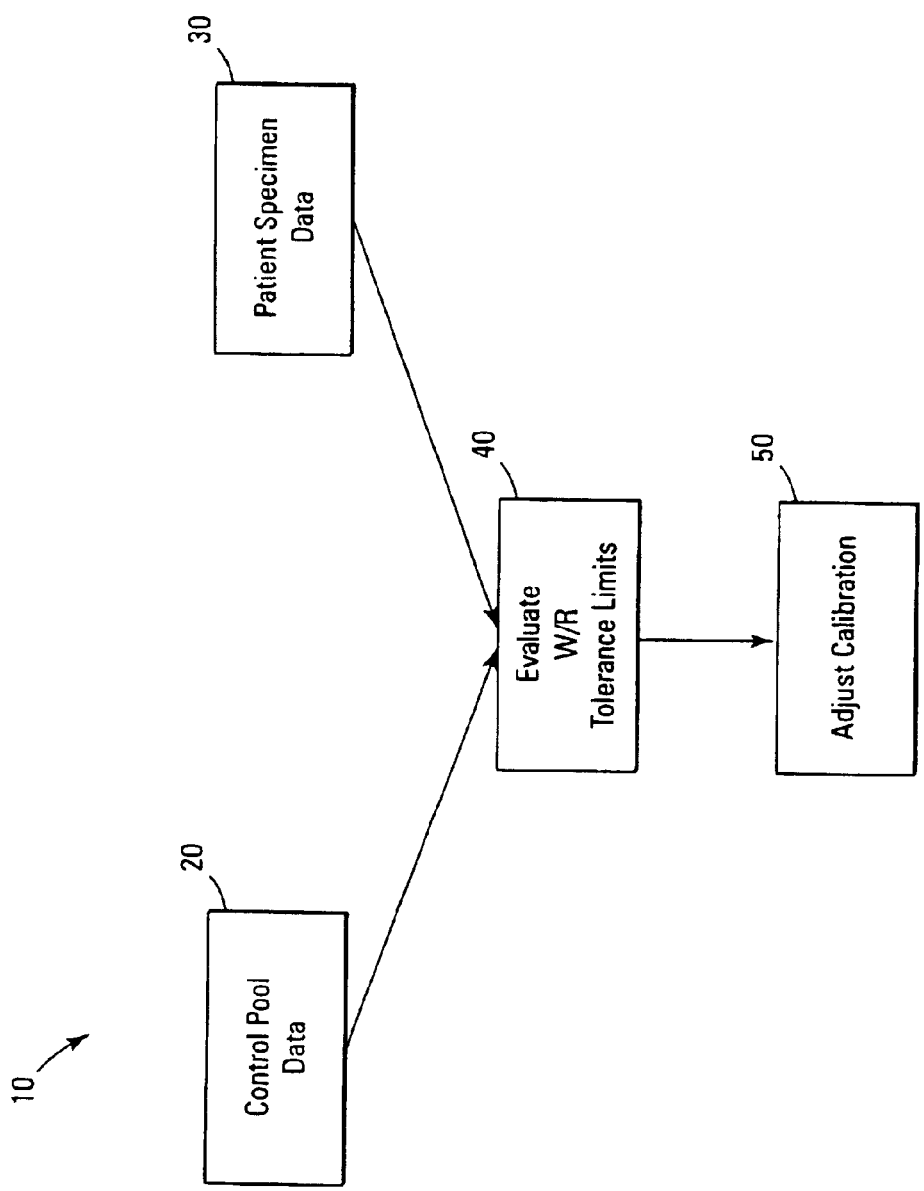
FIG. 1 is a flow diagram of a system implementing a method for calibrating a clinical laboratory analytical instrument.

The method of the invention may be used to periodically or continuously adjust the calibration of at least one clinical laboratory analytical instrument, referred to herein as a chemical analyzer. Referring to FIG. 1, the calibration method 10 of the invention evaluates analytic performance of the chemical analyzer with respect to two concurrent sources of data tracking information. In block 20, a commutable control pool is provided that include target analyte values for a particular assay (referred to herein as control pool data). In block 30, a distribution of test values derived from patient specimens is analyzed (referred to herein as patient specimen data). In block 40, the analytical performance of a chemical analyzer (or network of chemical analyzers) is evaluated with respect to predefined criteria, referred to herein as tolerance limits. If the results of both the control pool analysis information and the mathematical indices of patient values indicates a bias relative to the tolerance limits, then a calibration adjustment protocol in block 50 is activated to provide a calibration adjustment signal to the chemical analyzer (or network of chemical analyzers) and bring the test values closer to a known traceable reference.

Figure 2:
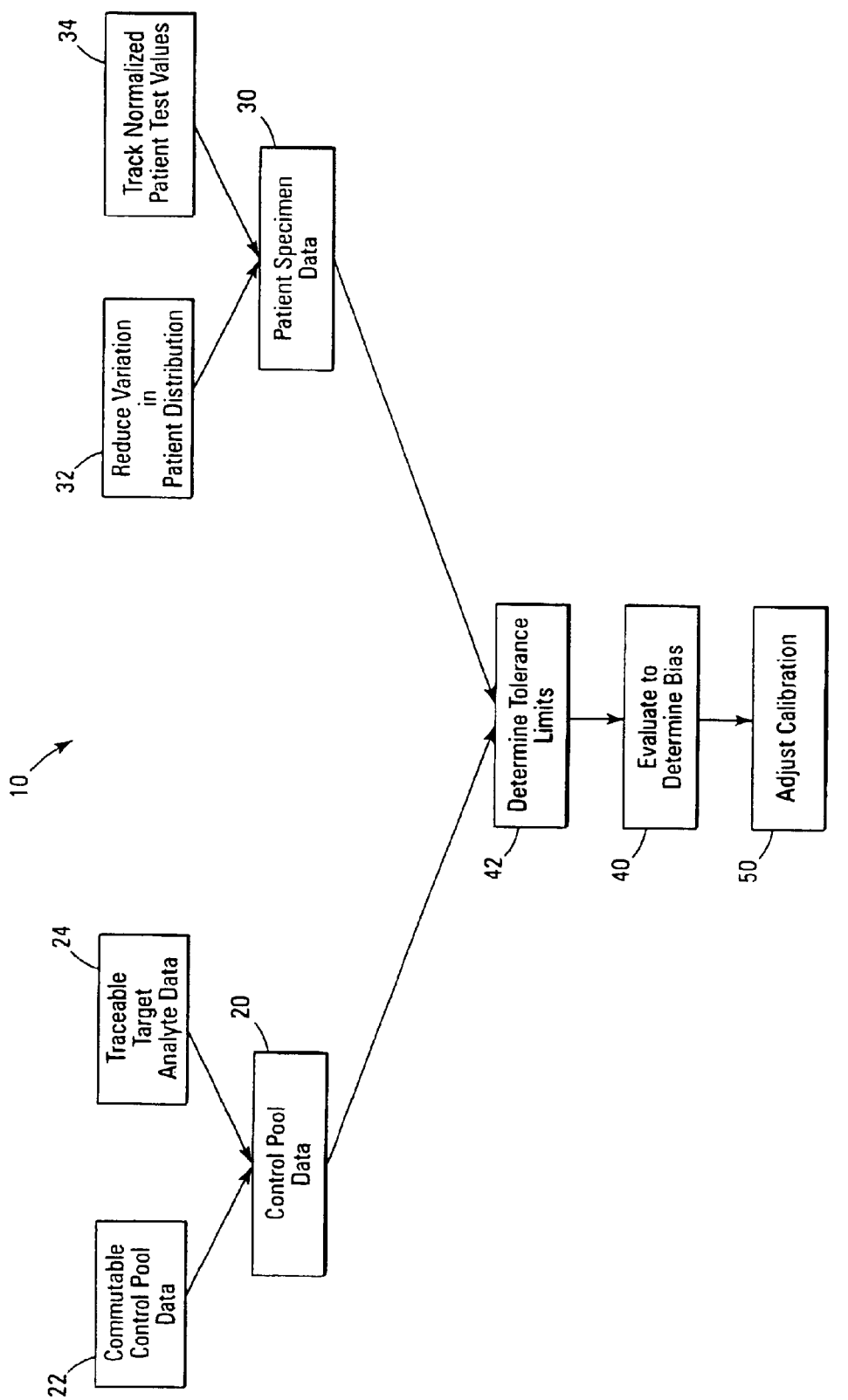
FIG. 2 is a flow diagram of a system implementing a method for calibrating a clinical laboratory analytical instrument.

Referring to FIG. 2, the calibration adjustment method preferably includes six components. Components (1) and (2) are used to generate the control pool data. Step (1) in block 22 includes providing control pool data that is commutable with the patient specimen data for a particular target analyte used in a laboratory assay, and step 2) in block 24 includes determining traceable target analyte values for the control pools. In steps (3)–(4) patient specimen data is generated and optionally mathematically analyzed to reduce data variance and improve the sensitivity of the calibration adjustment. In optional step (3) in block 32, variation in patient distribution is reduced, and in optional step (4) in block 34 normalized patient test values are tracked. In step (5) in block 42, tolerance limits are determined for the maximum allowable variation of the control pool data and the patient specimen data. In step (6) in block 40, the patient specimen data and the control pool data are compared, and if, based on the tolerance limits, a bias is detected, instructions are generated in block 50 to generate a calibration adjustment signal. The calibration adjustment signal adjusts the calibration of the chemical analyzer to more closely associate the assay target values in the analyzer to a known reference. Each of the components of the method will be discussed in turn.

1) Determining Commutable Control Pools

A clinical assay typically requires detection of at least one designated target analyte in a patient test sample. In the method of the invention, at least one calibrated standard laboratory analytical instrument is used to assign target values for the target analyte in a serum-based control pool. Suitable analytical instruments include, for example, atomic absorption spectrometers, such as those available from Perkin Elmer Instruments, Norwalk, Conn., under the trade designation Atomic Absorption Spectrometer 3300, and inductively coupled plasma atomic emission spectrometers.

Figure 3:
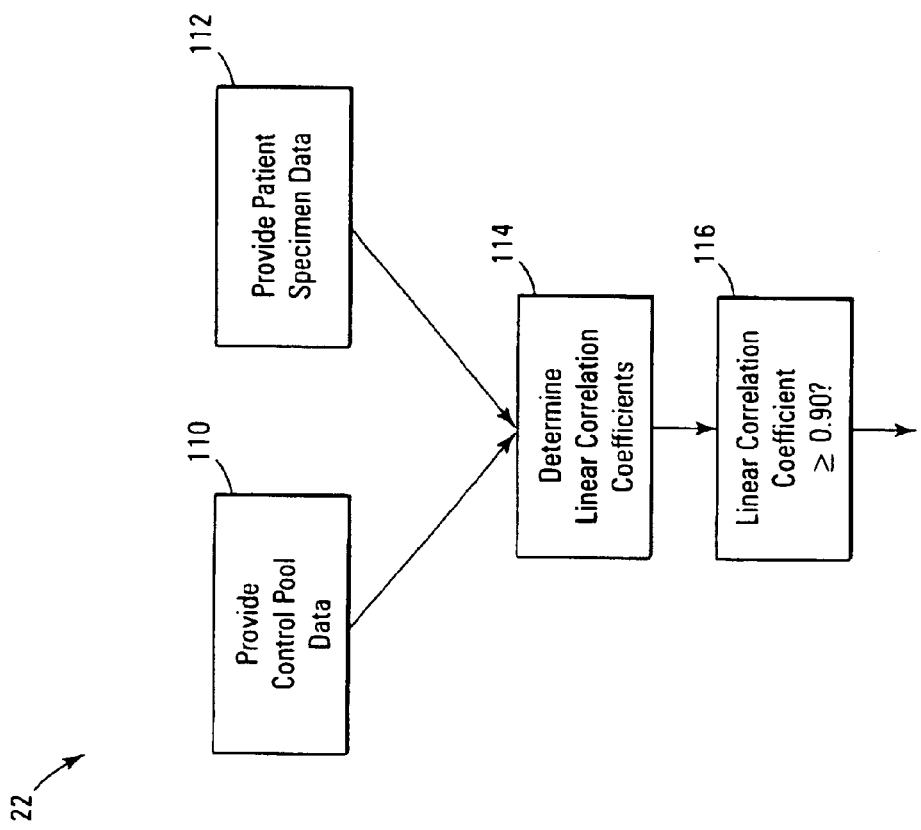
FIG. 3 is a flow diagram of a system implementing a method for providing control pool data.

Referring to FIG. 3, the control pools 110 include sera from large number of human subjects that are known to measure low, average or high values for the target analyte. The control pools may be obtained from commercial sources or produced from specimens previously tested in the laboratory. Suitable commercially available control pools include those available from Roche Diagnostics Corp., Indianapolis, Ind. under the trade designation Precitrol, and BioRad Laboratories, Irvine, Calif., under the trade designation Liquichek.

A collection of actual patient specimens 112 is then prepared and analyzed on a properly calibrated chemistry analyzer, and in block 114 it is determined whether the detected analyte values in the patient specimens are commutable with the analyte values in the control pools. A control pool is commutable with the actual patient specimens when the changes in the average of the patient test values for the target analyte correlates closely with the changes in the control pool values across an assay condition under consideration. Typically, as shown in block 116, a correlation coefficient between the control pool and the group of actual patient specimens of ≧ about 0.90, preferably ≧ about 0.95, more preferably ≧ about 0.99, indicates that the control pool and the specimens are commutable. To ensure accuracy, the collection of actual patient specimens preferably includes at least 20, preferably at least 100, specimens. Suitable clinical laboratory chemical analyzers include those available from Roche Diagnostics Corp., Indianapolis, Ind., under the trade designation Hitachi 747–200 Automatic Analyzer.

2) Traceable Target Values

Figure 4:
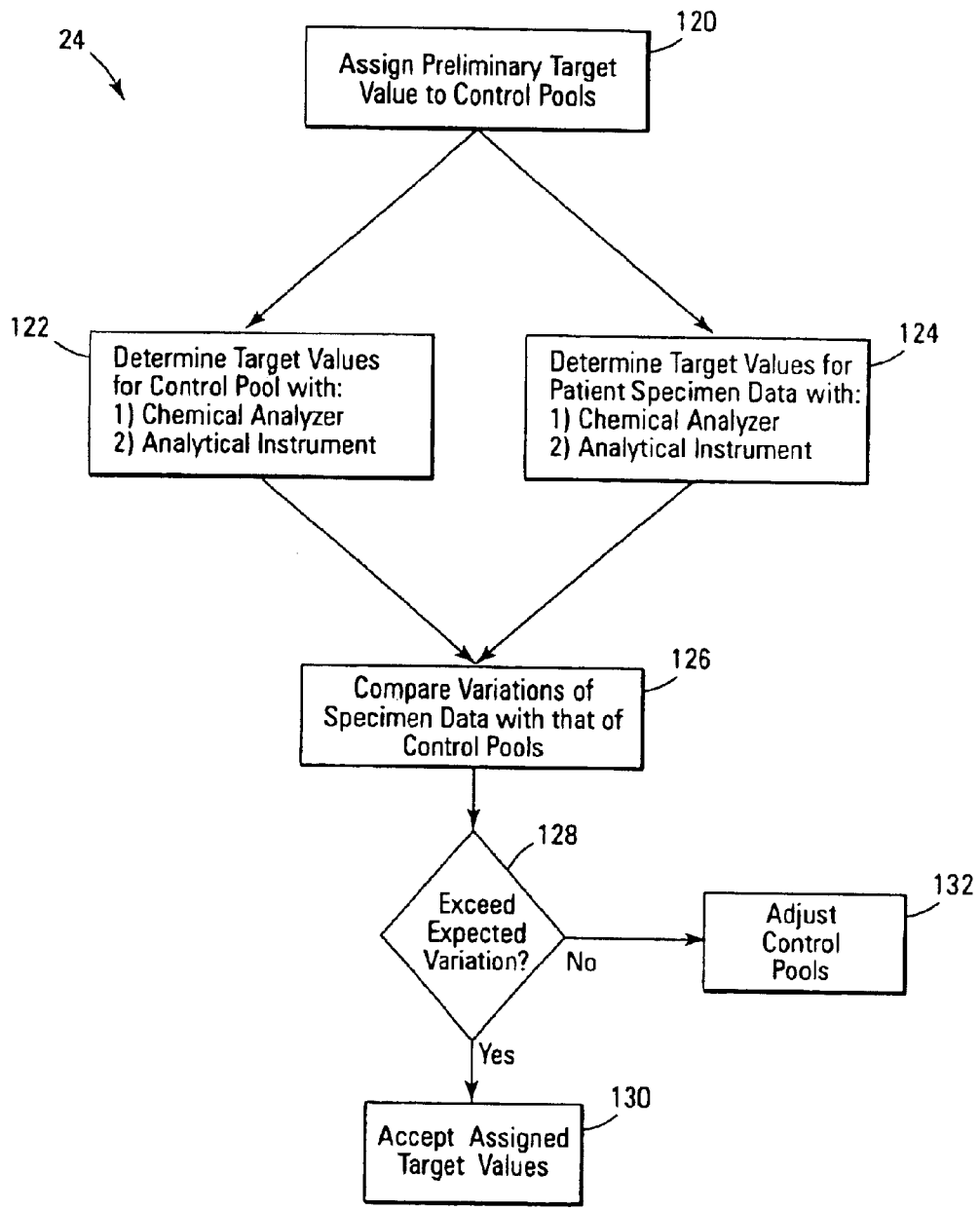
FIG. 4 is a flow diagram of a system for implementing a method for providing traceable target analyte data.

Referring to FIG. 4, target values for the analyte are assigned in block 120 to each control pool by analyzing the pools in replicate using an established reference method and setting the target value equal to the average of the replicate. This preliminary target value assignment is confirmed or adjusted based on the concordance of data collected from measuring a series of a number, preferably at least 10, more preferably at least 20, patient specimens concurrently with the control specimens on both the chemical analyzer and the reference analytical instrument. As shown in blocks 122, 124, the relationship between the target values for the control specimens from each of the chemical analyzer and the reference analytic instrument is compared in block 126 to the target values for the patient samples from each of the chemical analyzer and the analytical instrument. Referring to block 128, if the resultant differences match within the expected variation of the replicates, the assigned target values are accepted (block 130). If these differences exceed the expected variation, the assigned target values for the control pools are adjusted to bring them within a predetermined tolerance level for the designated assay (block 132).

3) Reducing Variation in Patient Distributions

Statistical techniques may be used to reduce the across specimen variation of the patient target values. For example, specimen identification information such as age, gender, and medical service area generally are available, as well as other patient specific information such as symptom presentation codes and results of other measurements. Multivariate regression analysis is a helpful tool for defining the association between these variables and the test values. Algorithms for correcting the patient test distributions for these differences can be defined by inverting the regression equations, and suitable commercial software packages are available from SAS Institute, Inc., Cary N.C.

4) Tracking the Normalized Distributions of Patient Test Values

To track the normalized distribution of target analyte test values, both the effective batch size and the choice of the tracking index for a selected distribution should be considered. The $50^{th}$ percentile can be estimated with tightest confidence, but other percentiles or estimation of percentage of patients exceeding key decision limits may have greater clinical utility. The larger the batch size, the smaller the intra-batch variance of the tracking index, but the longer the time interval it takes to detect changes. Moving windows and/or exponential smoothing functions with selected weighting factors can be developed which have large effective batch sizes, while still providing early detection of bias changes, as described in Smith, et al., *Optimal Procedures for Detecting Analytic Bias Using Patient Samples,* Am J. Clin. Pathol. 1997;108:254–268. For analytes with limited ranges and symmetric distributions (such as calcium) the average of the test values in the batch generally is an acceptable index for monitoring analytic bias.

5) Tolerance Limits For Monitoring the Traceable Control Pools and the Patient Distribution Indices Tolerance limits may be chosen by balancing the number of false positive signals with the sensitivity for detection of shifts for a selected assay. False positive limits can be defined by analyzing these monitoring indices during periods when the chemical analyzers are performing well. The sensitivity for error detection can be evaluated by examining these indices during periods when adverse changes have occurred. A multi-rule procedure such as described in Westgard and Klee, *Tietz Textbook of Clinical Chemistry,* $3^{rd}$ edition; 1998; pp 384–418, using predefined traceable target values and combinations of two controls outside warning limits or one control outside action limits is an effective way to balance error detection and specificity.

6) Adjusting the Calibration of the Chemical Analyzer

A calibration adjustment process is triggered when both a patient distribution index, which is determined from the procedures in steps (3)–(4) above, and at least one of a serum control rule, determined from the commutable control data determined in steps (1)–(2) above, exceed the warning and/or action limits (determined in step (5) above) in the same direction.

If calibration adjustment is required, a calibration signal is generated that adjusts the set-point of the calibrators for the chemical analyzer by an amount equal to the average difference between the assigned traceable target analyte values for the controls and the most recent measured target analyte values for the controls. A warning signal and or an advisory signal may be generated with, prior to or after the generation of the calibration signal. The target analyte values for the current batch of patient specimens and controls then are recalculated to modify the bias. The instrument operator may optionally be advised that calibration adjustment has occurred and may be asked to verify that the action was appropriate by examining the next batch of serum controls and patient indices.

The overall change in bias achieved by the calibration adjustment can be evaluated by calculating the residual root mean square (RMS) error of a commutable control pool not used in the adjustment process. The RMS error is calculated using the following equation:

$$\text{RMS Error} = \sqrt{\frac{\sum_{i=1}^{N}(x_i - x_{target})^2}{N-1}}$$

Where N=number of control values, $x_i$=measured values of the controls (observed concentration, both with and without calibration adjustment), and $x_{target}$=target values of the controls (concentrations assigned by the reference method).

Figure 5:
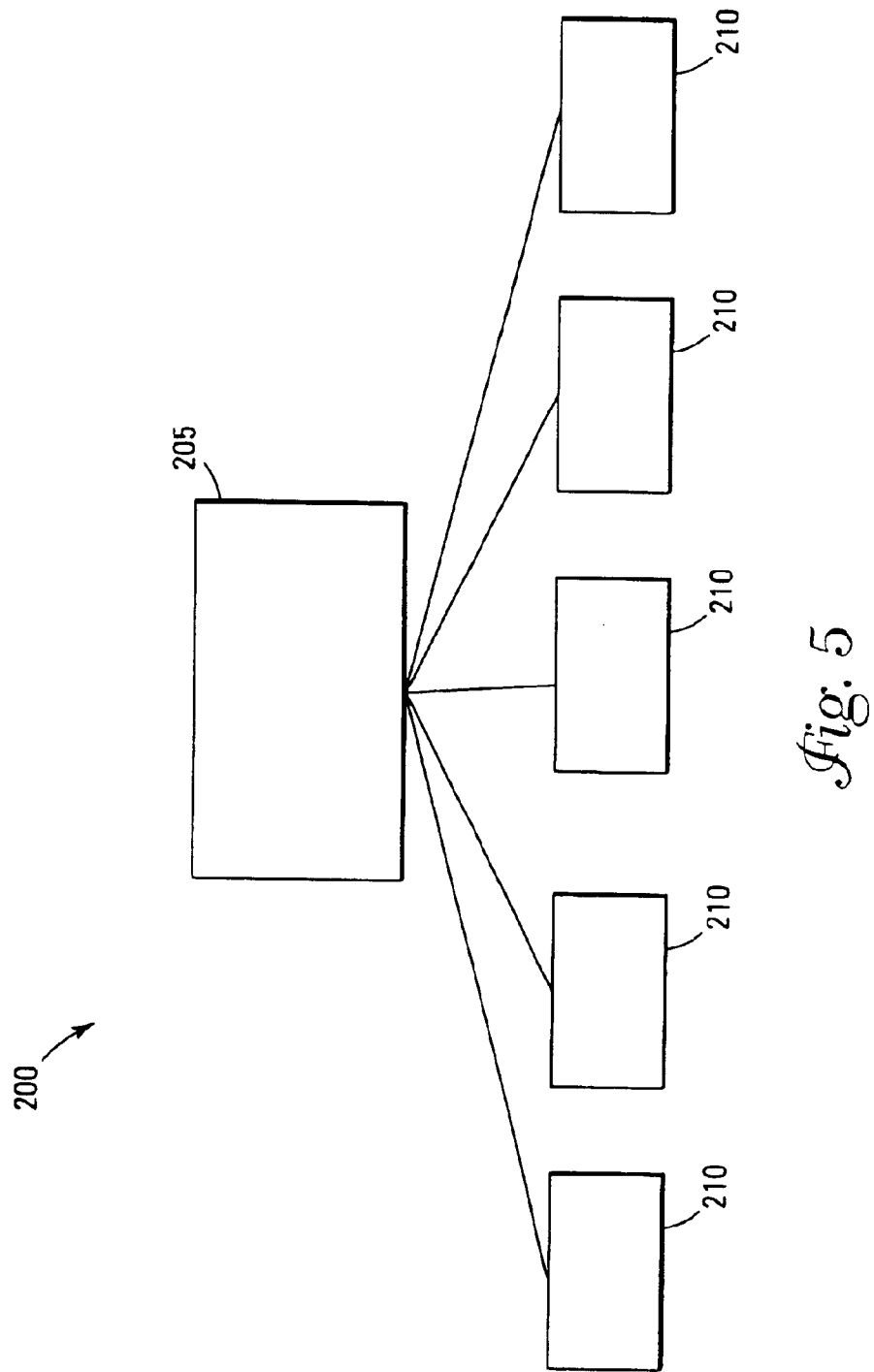
FIG. 5 is a functional block diagram of a clinical laboratory instrumentation system including a network of chemical analyzers.

Referring to FIG. 5, a chemical analyzer system 200 in a clinical laboratory may include an electrically interconnected network of chemical analyzers 210, each communicating with a central computer 205. Each chemical analyzer 210 may be configured to run a particular clinical assay, either automatically or under the control of an operator. The central computer and each chemical analyzer 210 may include a processor, a memory, an input device, and an output device. The memory may include random access memory (RAM) storing a program code that is accessed and executed by the processor.

The program code can be loaded into the memory from another memory device, such as a fixed hard drive or removable media device associated with system 200, the central computer 205, or with the analyzer 210. The program code stored in the memory can be arranged such that, when executed, a processor in the chemical analyzer 210 executes the calibration method of the invention to evaluate the analytical performance of the instrument and adjust its calibration, if necessary. The program code may also be executed by the central computer to evaluate the analytical performance of a particular chemical analyzer (or the entire network of chemical analyzers), and adjust their calibration, if necessary. In the alternative, the chemical analyzers may send assay data to the central computer periodically, and the central computer may continuously or periodically evaluate the analytical performance of any or all the chemical analyzers in the network.

The program code can be provided as a discrete application that is invoked by the user to analyze the analytical data. The application can be called by the push of a button, a mouse click, by voice, or via a network instruction.

The program code can be carried on a computer-readable data storage medium such as a fixed disk, a removable disk, or tape, and can be loaded into the memory of the central computer or the chemical analyzer for access and execution by the processor therein.

The method of the invention will now be discussed with reference to the following non-limiting examples.

EXAMPLES

The impact of small analytic bias changes on the number of patients having follow-up medical procedures is illustrated with three clinical examples: cholesterol testing to assess the risk of cardiovascular disease (Example 1), calcium testing for detection of hypercalcemia (Example 2) and prostate specific antigen (PSA) testing for the detection of prostate cancer (Example 3).

Example 1

Cholesterol Testing to Assess Risk of Cardiovascular Disease

Figure 6:
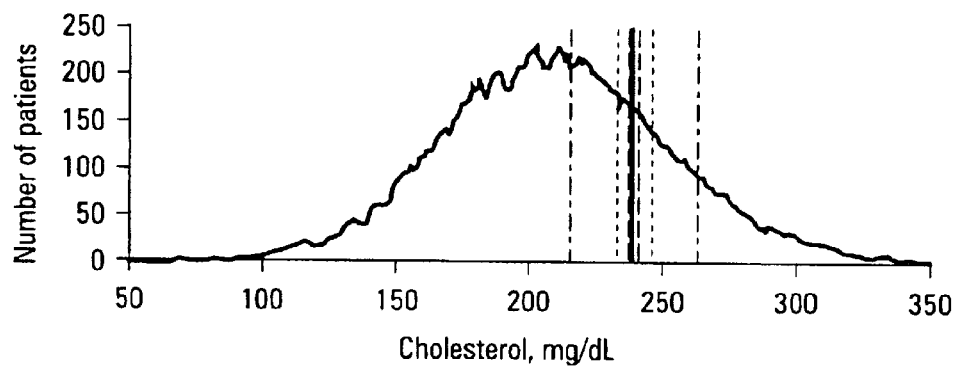
FIG. 6 is a plot of a cholesterol frequency distribution with ±1%, ±3% and ±10% limits around 240 mg/dl for Example 1.

The effect of analytic bias on patient classification is well illustrated in the measurement of cholesterol. The National Cholesterol Education Program (NCEP) recommends following up patients with cholesterol>260 mg/dL if they have no extra risk factors and following up patients with cholesterol>200 mg/dL if they have other risk factors (1). The distribution of cholesterol test values from 20,000 patients is illustrated in FIG. 6.

Table 1 shows the number and percentage of patients per 1000 that have values exceeding key decision points and the effect on analytic bias on these numbers. With a well calibrated assay, about 249 out of every 1,000 adult outpatients have values>240 mg/dL and 593 have values>200 mg/dL. If the assay shifts 3% upward, these numbers increase to 300 and 646, which represent increases of 20.5% and 8.8% over baseline. In tracking patient test distributions over time with a well-controlled assay, the test distributions change only about ±1.0% (2,3). This ±1% population variation corresponds to relatively tight ranges in the number of patients per thousand crossing the decision thresholds: 575 to 612 at the 200 mg/dL level and 234 to 263 at the 240 mg/dL level.

Therefore, analytic biases in a laboratory of ±3% can cause significant changes in the number of patients undergoing downstream medical procedures. Laboratory bias shifts of ±10% cause major changes in patient classifications.

TABLE 1

Cholesterol Bias Effects on Positives Per 1000

| Level | 200 mg/dL | | 240 mg/dL | |
|---|---|---|---|---|
| −10% bias | 410, | −31.0% | 120, | −51.8% |
| −3% bias | 538, | −9.4% | 203, | −18.5% |
| −1% bias | 575, | −3.2% | 234, | −6.0% |
| 0% bias | 594, | 0% | 249, | 0% |
| +1% bias | 612, | +3.0% | 263, | +5.6% |
| +3% bias | 646, | +8.8% | 300, | +20.5% |
| +10% bias | 759, | +27.8% | 446, | +79.1% |

Example 2

Measurement of Serum Calcium

The effect of analytic bias is illustrated in the measurement of Serum Calcium. Primary hyperparathyroidism (HPT) and malignancy are the major causes of hypercalcemia. The NIH consensus conference on Diagnosis and Management of Asymptomatic Primary HPT recommends that hypercalcemia be confirmed with repeat calcium measurement and followed up with intact parathyroid hormone (PTH) measurement (4).

Figure 7:
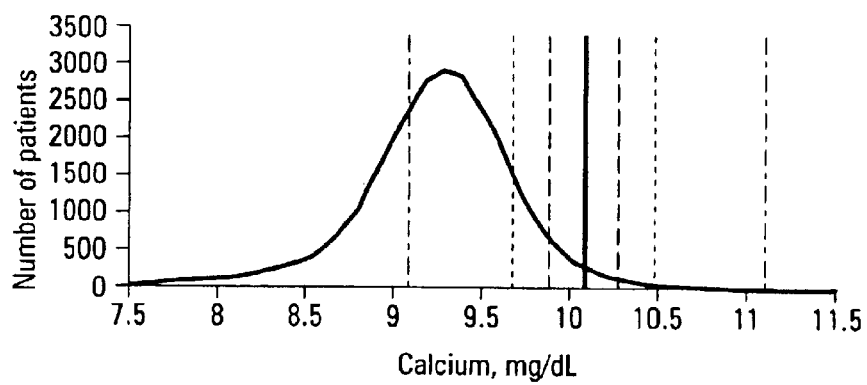
FIG. 7 is a plot of a calcium frequency distribution with ±2%, ±4% and ±10% limits around 10.1 mg/dl for Example 2.

FIG. 7 shows the frequency distribution of calcium values, along with decision limits set at the upper limit of normal (10.1 mg/dL). Other measurements such as 24 hour urinary calcium, ionized calcium and thyroid imaging may be needed to further investigate elevated PTH values.

FIG. 7 and the values in Table 2 show the very marked effect analytic bias has on the classification of hypercalcemia

TABLE 2

Calcium Bias Effects on Positives Per 1000

| Level | 10.1 mg/dL | | 10.4 mg/dL | |
|---|---|---|---|---|
| −10% bias | 2, | −92% | 1, | −90% |
| −4% bias | 7, | −72% | 4, | −60% |
| −2% bias | 13, | −52% | 6, | −40% |
| 0% bias | 25, | 0% | 10, | 0% |
| +2% bias | 52, | +108% | 18, | +80% |
| +4% bias | 113, | +352% | 36, | +260% |
| +10% bias | 640, | +2460% | 329, | +3190% |

Example 3

Prostate Specific Antigen Testing

A third example of analytical bias is seen in Prostate-Specific Antigen (PSA) Testing. The American Cancer Society and the American Urological Association recommend annual screening of men for prostate cancer using PSA and digital rectal examination beginning at age 50 years (or age 40 years for high-risk groups). The identification rates for detecting men at risk for prostate cancer depend on the cutoff value used for screening and the assay performance characteristics. Many programs recommend 4 ng/mL, whereas others recommend age-specific reference limits (7). We have used the reference limits of 4 ng/mL and 6 ng/mL for our analyses.

Figure 8:
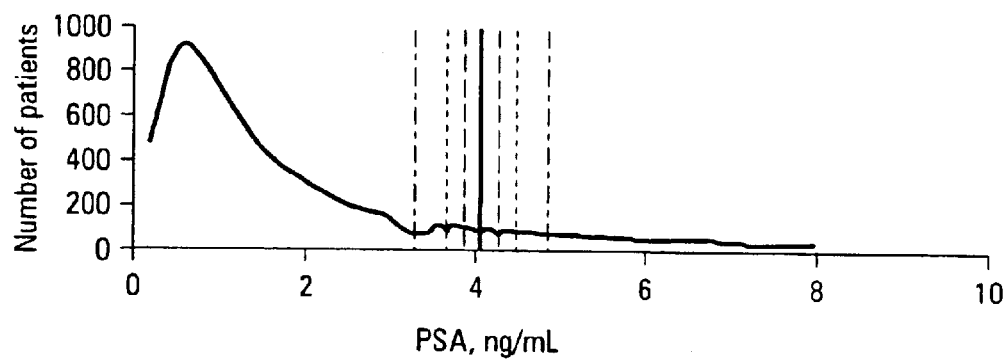
FIG. 8 is a PSA is a plot of a frequency distribution with ±6%, ±10% and ±20% limits around 4 ng/ml for Example 3.

The frequency distribution for 20,000 PSA tests run at the Mayo Clinic are shown in FIG. 8, along with lines to show the variations small analytic changes can produce in the percentage of patients crossing a key decision threshold (4.0 ng/mL). Table 3 further illustrates how these analytic bias differences translate into the number of patients per 1000 that may require further testing and prostate biopsy.

TABLE 3

PSA Bias Effects on Positives Per 1000

| Level | 4.0 ng/mL | | 6.0 ng/mL | |
|---|---|---|---|---|
| −20% bias | 144, | −18.2% | 87, | −21.6% |
| −10% bias | 160, | −9.1% | 98, | −11.7% |
| −6% bias | 165, | −6.3% | 103, | −7.2% |
| 0% bias | 176, | 0% | 111, | 0% |
| +6% bias | 184, | +4.5% | 119, | +7.0% |
| +10% bias | 196, | +11.4% | 126 | +13.5% |
| +20% bias | 220, | +25.0% | 144, | +29.7% |

Example 4
Prospective Validation Data

This inventive method and proposed analytical system was validated using the data collected from serum calcium measurements on two Roche Hitachi 747 chemistry analyzers. The reference procedure for assigning target values for the serum controls was atomic absorption spectroscopy. Three lot numbers of reagents were utilized (Roche #616-042-01, #615-422-01 and #145-500). Also six serum-based quality control pools (BioRad Liquichek Level 1, Lot No. #N16161, Liquichek Level 2, Lot No. #H16162, Roche Precitrol N, Lot No. #19950101, and Roche Precitrol A, Lot No. #19979701 plus two in-house pools of patient specimens) were measured with each batch of specimens.

A total of 1800 patient specimens were aliquoted into six replicate tubes and frozen at −20 ° C. for 5 to 30 days prior to analysis. All 1800 specimens were analyzed on two Hitachi 747 instruments (Serial #0821-3 and #0922-2), using three different lots of reagents on each instrument.

The patient specimens were run in batches of 450. Prior to analyzing each batch, the instruments were calibrated using CFAS calibrator lot #15272401. Immediately after instrument calibration, two additional lots of calibrators were analyzed and recorded (CFAS lot #19960801 and #19984701). These other calibrators were used to recalculate the patient test results using the derived optical density measurements.

The net effect of this processing was to produce 1800 patient values and 24 control values measured 18 ways (2 instruments×3 reagent lots×3 calibrators). The patient data and the four commercial controls were used for the calibration adjustment protocol. The replicate measurements of the two control pools made from residual sera were used to evaluate the reduction in the RMS error attributable to the calibration adjustment process. The overall RMS error of the measured values for these two patient sera pools for all 18 assay conditions can be compared to the RMS error of the recalculated values for these controls using the results from the calibration adjustment process. Since these two control pools were made from actual human specimens, the reduction in their errors are representative of the reduction in the bias errors of the patient values.

A. Commutability of Control Pools

Figure 9:
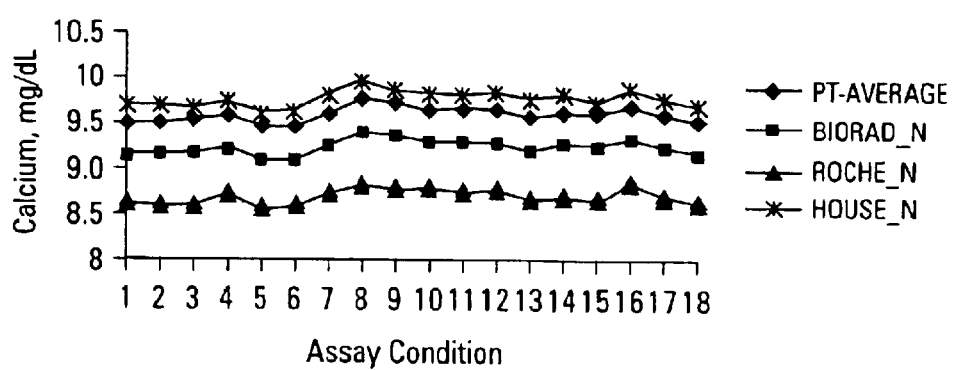
FIG. 9 is a plot of commutablity of control pools for the values of Example 4.

FIG. 9 shows the mean of the patient test values tracks closely with the average of the three normal controls when plotted sequentially, according to the 18 test conditions. Similar data were obtained for the high controls. The respective linear correlation coefficients for BioRad N, BioRad H, Roche N, and Roche H control pools were: 0.99, 0.96, 0.94, and 0.93. These high correlation coefficients show that all four commercial controls are commutable with the changes found in the patient values. In addition, the linear correlation coefficients for the two in-house pools were 0.96 and 0.92, showing that they also were commutable.

B. Assigning Traceable Target Values to Pools

Figure 10:
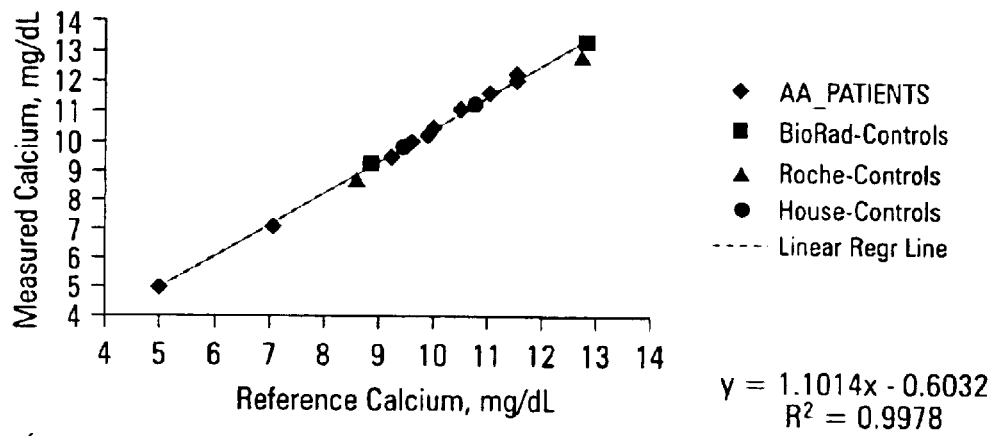
FIG. 10 is a plot of a traceability assignment for the values of Example 4.

The preliminary target values assigned to the pools were: BioRad N=8.9 mg/dL, Roche N=8.6 mg/dL, BioRad H=12.9 mg/dL, and Roche H=12.8 mg/dL. FIG. 10 shows a cross plot of the average measured values for 10 patient specimens versus their assigned atomic absorption concentrations. FIG. 10 also shows that the average measured values for five of the control pools have the same offset from their reference values as was found with the patient specimens. Therefore, the traceable targets for these pools were accepted. However, one control, the Roche H-pool designated by the upper triangle, had a different offset. The target value for this control was adjusted down from 12.8 to 12.3 mg/dL.

The final traceable target values for the pools were: BioRad N=8.9 mg/dL, Roche N=8.6 mg/dL, BioRad H=12.9 mg/dL, and Roche H=12.3 mg/dL.

C. Algorithm to Reduce Variation Across Patient Values

Multivariate regression, using the statistical package available from SAS Institute, Cary, N.C., on a group of 50,000 test values, showed that patient calcium concentrations had significant ($p<0.001$) statistical relationships with gender, and patient age. Also the following medical service areas showed significant differences—Endocrinology ($p<0.001$), Nephrology ($p=0.05$), and Hospitalization ($p<0.001$).

The multivariate regression equation was:

Calcium, mg/dL=9.56

+0.094*Gender (0=M, 1=F)

−0.00784*Age (yrs)

+0.0000588*Age$^2$ (yrs)

+0.04903*Endo. (∅=No, 1=Yes)

−0.05389*Neph. (∅=No, 1=Yes)

−0.3160*Hosp. (∅=No, 1=Yes)

These equations were inverted to give the following algorithm for normalization of the calcium test values used in the calibration adjustment system.

Normalized Calcium=Original Calcium

−0.094*Gender

+0.00784*Age

−0.00005885*Age$^2$

−0.04902716*Endo.

+0.053389*Neph.

+0.3160*Hosp.

D. Algorithm For Tracking Changes in Patient Values

Figure 11:
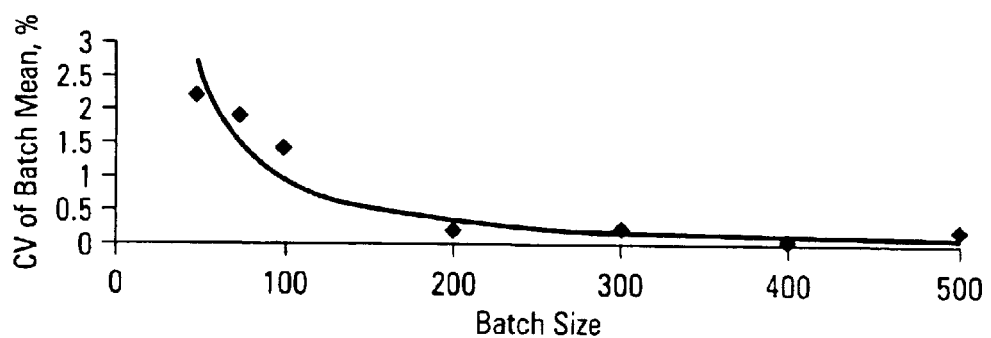
FIG. 11 is a plot of coefficient of variation of patient values as a function of batch size for the values of Example 4.

FIG. 11 shows that the across-batch coefficient of variation for the average calcium concentration for the patients in the batch decreases exponentially with batch size. Based on these data, the batch size for tracking the patient calcium values was set at 100. The average calcium concentration for these batches of 100 specimens was chosen as the tracking index.

E. Tolerance Limits For Monitoring Pools and Patient Indices

The average within run CV's for the four commercial controls were 1.01%, 0.60%, 0.53%, 0.62%, for BioRad N, BioRad H, Roche N and Roche H respectively when the assay was stable. The within run CV for the across-batch average of patient calcium concentrations with a batch size of 100 was about 1.0%. However, when these controls were evaluated relative to the reference target values the CV's were larger, so wider monitoring limits were established.

The warning and action limits for the controls and the monitoring index for the 100 specimen batches of patient values were established (in units of mg/dL) as:

| Control | Target | Warning Limits | Action Limits |
|---|---|---|---|
| BioRad-N | 8.9 | 8.6, 9.2 | 8.4, 9.4 |
| BioRad-H | 12.9 | 12.6, 13.2 | 12.4, 13.4 |
| Roche-N | 8.6 | 8.3, 8.9 | 8.1, 9.1 |
| Roche-H | 12.3 | 12.0, 12.6 | 11.8, 12.8 |
| Patient Ave | 9.4 | 9.0, 9.8 | 8.8, 10.0 |

The criteria for calibration adjustment was when two of the control pools from the current batch or the previous batch exceeded the warning limits in the same direction or one pool exceeded the action limits and the patient average index was outside the warning limits in the same direction in both the current batch and the previous batch or the patient average index for the current batch was outside the action limits in the same direction.

F. Calibration Adjustment Controller

Figure 12:
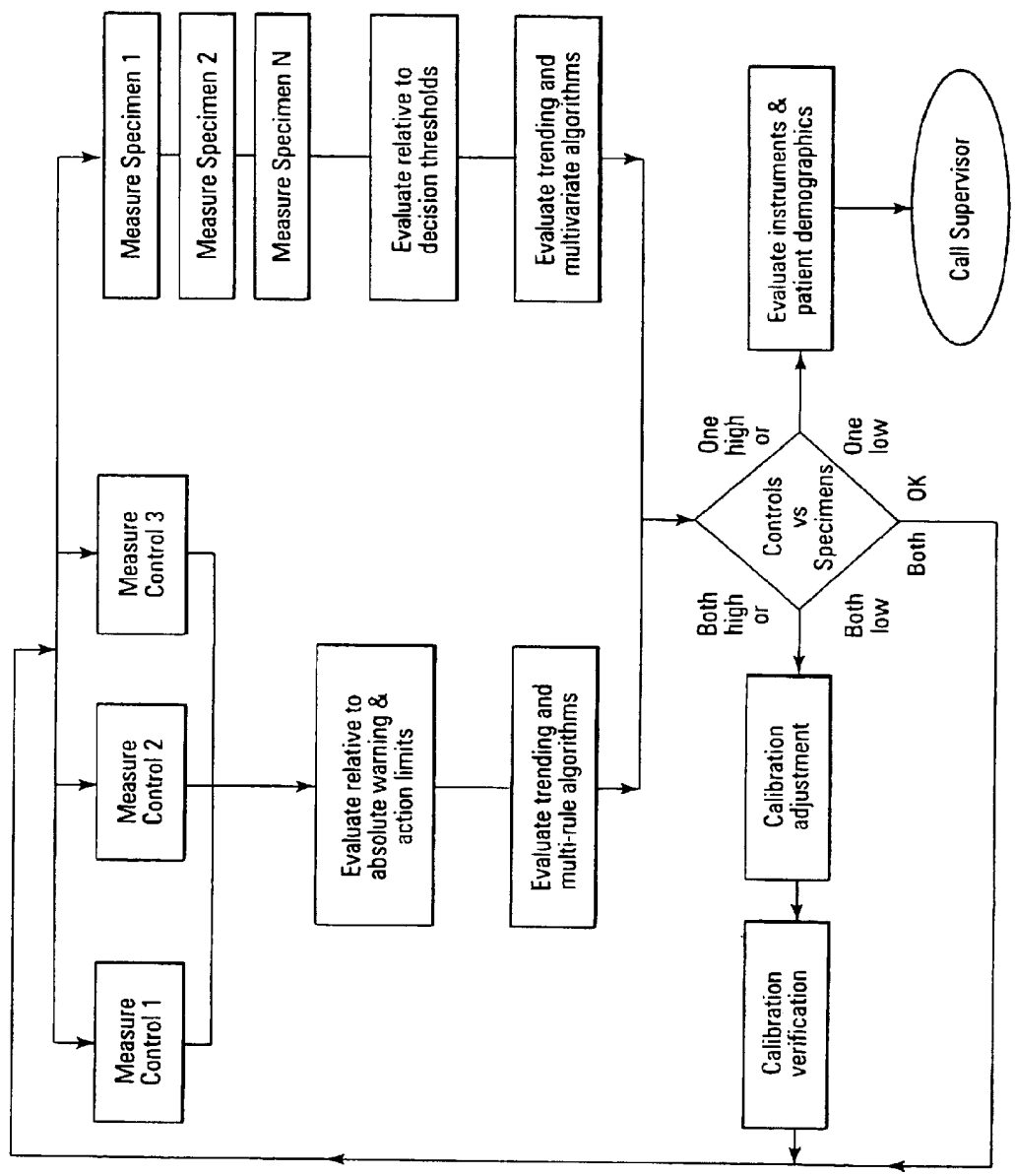
FIG. 12 illustrates the calibration adjustment method.

FIG. 12 illustrates the calibration adjustment process. Both control pools and the patient value index are monitored using the algorithms and limits defined in items (a) through (e). When both the control pools and the patient index showed a major bias, the calibration was adjusted. In the measurement of the 35,000 patient specimens and controls, 32 calibration adjustments were made. These assay calibration adjustments reduced the RMS residual error of the normal control pool by 57% and the RIMS residual error of the high control pool by 72%.

A number of embodiments of the invention have been described. Nevertheless, it will be understood that various modifications may be made without departing from the spirit and scope of the invention. Accordingly, other embodiments are within the scope of the following claims.

What is claimed is:

1. A method for calibrating a clinical laboratory analytical instrument, comprising:
    generating control pool data from a commutable control pool, wherein the control pool has target analyte values for an assay;
    generating patient specimen data from a distribution of test values for the target analyte from patient specimens;
    determining tolerance limits from the control pool data and the patient specimen data; and
    adjusting the calibration of the instrument with respect to the tolerance limits.

2. The method of claim 1, further comprising reducing variation in the patient specimen data prior to determination of the tolerance limits.

3. The method of claim 2, further comprising tracking a normalized distribution the patient specimen data prior to determination of the tolerance limits.

4. The method of claim 1, further comprising tracking a normalized distribution of the patient specimen data prior to determination of the tolerance limits.

5. The method of claim 1, wherein the tolerance limits comprise at least one of warning limits and action limits.

6. The method of claim 1, wherein the adjusting step comprises generating a calibration control signal.

7. The method of claim 1, wherein said control pool has at least one target analyte with corresponding target analyte for an assay, and wherein patient specimen data is generated from a distribution of test values for each matching analyte.

8. The method of claim 7, further comprising tracking a normalized distribution of the patient specimen data for each analyte prior to determination of the tolerance limits.

9. A method for calibrating a clinical laboratory instrument, comprising:
    (a) generating a serum control rule by:
        (i) providing a control pool that is commutable with patient specimen data for a particular target analyte used in an assay, and
        (ii) determining traceable target analyte values for the control pool;
    (b) generating a patient distribution index by:
        (i) reducing variation in a patient distribution, and
        (ii) tracking normalized patient test values for the target analyte;
    (c) determining tolerance limits for the maximum allowable variation of the serum control rule and the patient distribution index;
    (d) comparing the patient distribution index and the serum control rule to detect a bias with respect to the tolerance limits; and
    (e) adjusting the calibration of the instrument to modify the bias.

10. A computer readable medium encoded with a computer program, the program being arranged such that, when the program is executed, a computer performs acts comprising:
    generating control pool data from a commutable control pool, wherein the control pool has target analyte values for an assay;
    generating patient specimen data from a distribution of test values for the target analyte from patient specimens;
    determining tolerance limits from the control pool data and the patient specimen data; and
    adjusting the calibration of an instrument with respect to the tolerance limits.

11. The computer readable medium of claim 10, wherein said acts further comprise:
    reducing variation in the patient specimen data prior to determination of the tolerance limits.

12. The computer readable medium of claim 11, wherein said acts further comprise:
    tracking a normalized distribution of the patient specimen data prior to determination of the tolerance limits.

13. The computer readable medium of claim 10, wherein said acts further comprise:
    tracking a normalized distribution of the patient specimen data prior to determination of the tolerance limits.

14. The computer readable medium of claim 10, wherein the tolerance limits comprise at least one of warning limits and action limits.

15. The computer readable medium of claim 10, wherein adjusting comprises generating a calibration control signal.

16. The computer readable medium of claim 10, wherein said acts further comprise:
    generating an advisory with a calibration control signal.

17. The computer readable medium of claim 10, wherein said acts further comprise:
    determining the efficacy of adjusting the calibration with respect to the tolerance limits.

18. The computer readable medium of claim 17, wherein determining the efficacy comprises calculating a residual root mean square (RMS) error.

19. A chemical analyzer comprising a processor responsive to a computer program, the program being arranged such that, when the program is executed, the processor performs acts comprising:

generating control pool data from a commutable control pool, wherein the control pool has target analyte values for an assay;

generating patient specimen data from a distribution of test values for the target analyte from patient specimens;

determining tolerance limits from the control pool data and the patient specimen data; and adjusting the calibration of an instrument with respect to the tolerance limits.

20. The analyzer of claim 19, said acts further comprising:

reducing variation in the patient specimen data prior to determination of the tolerance limits.

21. The analyzer of claim 20, said acts further comprising:

tracking a normalized distribution of the patient specimen data prior to determination of the tolerance limits.

22. The analyzer of claim 19, said acts further comprising:

tracking a normalized distribution of the patient specimen data prior to determination of the tolerance limits.

23. The analyzer of claim 19, wherein the tolerance limits comprise at least one of warning limits and action limits.

24. The analyzer of claim 19, wherein adjusting the calibration comprises generating a calibration control signal.

25. The analyzer of claim 24, further comprising generating an advisory with the calibration control signal.

26. The analyzer of claim 19, further comprising determining the efficacy of adjusting the calibration with respect to the tolerance limits.

27. The analyzer of claim 26, wherein determining the efficacy comprises calculating a residual root mean square (RMS).

28. A clinical analytical instrumentation system, comprising a central computer and a network of chemical analyzers, wherein at least one of the central computer and the analyzers comprise a processor responsive to a computer program, the program being arranged such that, when the program is executed, the processor performs acts comprising:

generating control pool data from a commutable control pool, wherein the control pool has target analyte values for an assay;

generating patient specimen data from a distribution of test values for the target analyte from patient specimens;

determining tolerance limits from the control pool data and the patient specimen data; and adjusting the calibration of a chemical analyzer with respect to the tolerance limits.

29. A method for analyzing data in an analytical laboratory, wherein the laboratory comprises a central computer networked with at least one chemical analyzer, the method comprising:

transferring assay data from the analyzers to the central computer, wherein a processor in the central computer:

generates control pool data from a commutable control pool, wherein the control pool has target analyte values for an assay;

generates patient specimen data from a distribution of test values for the target analyte from patient specimens;

determines tolerance limits from the control pool data and the patient specimen data; and adjusts the calibration of at least one chemical analyzer with respect to the tolerance limits.

30. A method for calibrating a clinical laboratory analytical instrument, comprising:

generating a serum control rule from a commutable control pool, wherein the control pool has target analyte values for an assay;

generating a patient distribution index from patient specimens;

determining tolerance limits from the serum control pool and the patient distribution index; and adjusting the calibration of the instrument with respect to the tolerance limits.

* * * * *

UNITED STATES PATENT AND TRADEMARK OFFICE
CERTIFICATE OF CORRECTION

PATENT NO. : 6,787,361 B1
DATED : September 7, 2004
INVENTOR(S) : George G. Klee It is certified that error appears in the above-identified patent and that said Letters Patent is hereby corrected as shown below:

<u>Title page,</u>
Item [56], References Cited, OTHER PUBLICATIONS, "Westgard et al. reference", please delete "3th" and insert -- $3^{rd}$ -- therefor;

<u>Column 13,</u>
Line 32, after "(RMS)", please insert -- error --.

Signed and Sealed this

Seventeenth Day of May, 2005

JON W. DUDAS
*Director of the United States Patent and Trademark Office*